United States Patent
Wright et al.

(10) Patent No.: US 11,917,515 B2
(45) Date of Patent: Feb. 27, 2024

(54) ALLERGEN WARNING SYSTEM AND METHOD

(71) Applicant: KONINKLIJKE PHILIPS N.V., Eindhoven (NL)

(72) Inventors: Christopher John Wright, Lausanne (CH); Matthew John Lawrenson, Lausanne (CH); Julian Charles Nolan, Pully (CH); Vincentius Paulus Buil, Veldhoven (NL); Lucas Jacobus Franciscus Geurts, Sterksel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 606 days.

(21) Appl. No.: 17/056,440

(22) PCT Filed: Jun. 6, 2019

(86) PCT No.: PCT/EP2019/064839
§ 371 (c)(1),
(2) Date: Nov. 18, 2020

(87) PCT Pub. No.: WO2019/234178
PCT Pub. Date: Dec. 12, 2019

(65) Prior Publication Data
US 2021/0211856 A1  Jul. 8, 2021

(30) Foreign Application Priority Data
Jun. 7, 2018  (EP) ..................................... 18176413

(51) Int. Cl.
*H04W 4/90* (2018.01)
*A61B 5/00* (2006.01)
(Continued)

(52) U.S. Cl.
CPC ............. *H04W 4/90* (2018.02); *A61B 5/0022* (2013.01); *A61B 5/1112* (2013.01); *A61B 5/411* (2013.01);
(Continued)

(58) Field of Classification Search
CPC ..... A61B 5/0022; A61B 5/1112; A61B 5/411; A61B 5/7275; A61B 5/746; A61B 5/08;
(Continued)

(56) References Cited

U.S. PATENT DOCUMENTS

| 7,366,588 B2 | 4/2008 | Kim |
| 9,375,847 B2 | 6/2016 | Angle |

(Continued)

FOREIGN PATENT DOCUMENTS

| CN | 105353791 | | 2/2016 |
| CN | 106815477 | A | 6/2017 |

(Continued)

OTHER PUBLICATIONS

International Search Report and Written Opinion dated Sep. 4, 2019 For International Application No. PCT/EP2019/064839 Filed Jun. 6, 2019.

(Continued)

*Primary Examiner* — Ojiako K Nwugo
(74) *Attorney, Agent, or Firm* — Maschoff Brennan

(57) ABSTRACT

A system and method are provided for warning of an exposure of a second individual to an allergen by transfer from a first individual. Movements of the individuals are tracked so that allergen types and levels to which the individuals have been exposed can be obtained. Using knowledge of user sensitivity information to different allergens, it is determined if the first individual has been exposed to allergen types and levels which pose a risk to the second individual by GPS transfer from the first individual to the (Continued)

second individual. Thus, action can be taken when there is a determined risk of allergen transfer between individuals.

15 Claims, 3 Drawing Sheets

(51) Int. Cl.
| | | |
|---|---|---|
| *A61B 5/11* | (2006.01) | |
| *F24F 11/52* | (2018.01) | |
| *G01N 33/00* | (2006.01) | |
| *G16H 10/65* | (2018.01) | |
| *G16H 40/67* | (2018.01) | |
| *G16H 50/30* | (2018.01) | |
| *H04W 4/029* | (2018.01) | |
| *A61B 5/08* | (2006.01) | |

(52) U.S. Cl.
CPC ............ *A61B 5/7275* (2013.01); *A61B 5/746* (2013.01); *F24F 11/52* (2018.01); *G01N 33/0063* (2013.01); *G01N 33/0075* (2013.01); *G16H 10/65* (2018.01); *G16H 40/67* (2018.01); *G16H 50/30* (2018.01); *H04W 4/029* (2018.02); *A61B 5/08* (2013.01); *A61B 2560/0242* (2013.01)

(58) Field of Classification Search
CPC ......... A61B 2560/0242; A61B 5/6898; H04W 4/90; H04W 4/029; H04W 4/02; F24F 11/52; G01N 33/0063; G01N 33/0075; G01N 2001/021; G16H 10/65; G16H 40/67; G16H 50/30
See application file for complete search history.

(56) References Cited

U.S. PATENT DOCUMENTS

| | | | |
|---|---|---|---|
| 2012/0286959 A1 | 11/2012 | Ray et al. | |
| 2014/0213925 A1* | 7/2014 | Chan | A61B 7/003 600/595 |
| 2015/0153317 A1 | 6/2015 | Krebs | |
| 2016/0091474 A1* | 3/2016 | Griffon | G01N 33/0036 702/24 |
| 2017/0024531 A1* | 1/2017 | Malaviya | G16H 50/30 |
| 2017/0124839 A1 | 5/2017 | Weissman | |
| 2018/0120274 A1* | 5/2018 | Roseway | G01N 31/224 |
| 2018/0263494 A1* | 9/2018 | Yoo | A61B 5/0022 |
| 2018/0322255 A1* | 11/2018 | Connell, II | G16H 50/30 |
| 2019/0004023 A1* | 1/2019 | Kelly | G01D 3/08 |
| 2019/0099122 A1* | 4/2019 | Kaur | A61B 5/1459 |
| 2022/0293278 A1* | 9/2022 | Correnti | G06V 40/172 |

FOREIGN PATENT DOCUMENTS

| | | |
|---|---|---|
| CN | 107106956 A | 8/2017 |
| CN | 107211025 A | 9/2017 |
| JP | 2007026393 A | 2/2007 |
| JP | 2017148210 A | 8/2017 |
| KR | 20150075161 A | 7/2015 |
| WO | 2014122943 | 8/2014 |
| WO | 2014207629 | 12/2014 |
| WO | 2017/148876 | 9/2017 |

OTHER PUBLICATIONS

Jantunen, et al: "Pollen transport by clothes", Aerobiologia vol. 27, pp. 339-343(2011).
McDonagh: "The influence of human physical activity and contaminated clothing on particle resuspension", Nov. 2013, Journal of Environmental Radioactivity 127C:119-126.
Zhang, et al.: "A Review of Fabric Identification Based on Image Analysis Technology", 2014 https://archive.org/details/AReviewOfFabricIdentificationBasedOnImageAnalysisTechnology.
McCann, "New app sets sights on allergy sufferers", Feb. 5, 2013.
Richard Gray:"Which pollen is making YOU sneeze? Graphic identifies the source of your allergy to help you manage hayfever misery", MAILONLINE, 2015 https://www.dailymail.co.uk/sciencetech/article-3099648/Which-pollen-making-sneeze-Graphic-identifies-source-allergy-help-manage-hayfever-misery.html.
Romain Dillet: "Plume Labs' Flow is an air quality tracker to avoid pollution", Jan. 2017, https://techcrunch.com/2017/01/03/plume-labs-flow-is-an-air-quality-tracker-to-avoid-pollution/.
Dan Howarth: "TZOA wearable environment tracker measures UV and air pollution", Nov. 2014 https://www.dezeen.com/2014/11/26/woke-studios-tzoa-wearable-evironment-tracker-measures-uv-air-pollution/.
Natalija Knaidele: "Zyrtec App Gamifies Allergy Diagnosis", Jun. 2014 http://www.gamification.co/2014/06/03/zyrtec-gamifies-allergies-better-allergy-maintenance/.
Ian Ozsvald: "Allergic Rhinitis ("Why do I always sneeze ?! ") research project using Machine Learning", Data science Life PythonJan. 11, 2016 http://ianozsvald.com/2016/01/11/allergic-rhinitis-why-do-i-always-sneeze-research-project-using-machine-learning/.
Pablo Valerio: "MIT WiFi Technology Promises Precise Location Tracking", May 2016 http://www.networkcomputing.com/wireless-infrastructure/mit-wifi-technology-promises-precise-location-tracking/1586154916.
Massachusetts Institute of Technology: "WiTrack Through-Wall 3D Tracking Using Body Radio Reflections" 2014 http://witrack.csail.mit.edu/.
Wikipedia: "Wi-Fi positioning system" https://en.wikipedia.org/wiki/Wi-Fi_positioning_system.
Google: "ARCore overview" https://developers.google.com/ar/discover.
Amanda Macmillan: "20 Sneaky Spots Where Allergy Triggers Hide", Mar. 2016 http://www.health.com/home/places-pollen-can-hide.
John Farrier: "High Tech Doormat Sucks the Dirt off Your Shoes", Jun. 2012 http://www.neatorama.com/2012/06/21/high-tech-doormat-sucks-the-dirt-off-your-shoes/.
Karami, et al: "User in the Loop: Adaptive Smart Homes Exploiting User Feedback—State of the Art and Future Directions", Information 2016, 7(2), 35 http://www.mdpi.com/2078-2489/7/2/35/htm.
Nazerfard, et al: "Using Bayesian Networks for Daily Activity Prediction", Plan, Activity, and Intent Recognition: Papers from the AAAI 2013 Workshop http://www.aaai.org/ocs/index.php/WS/AAAIW13/paper/viewFile/7009/6592.
Jim Martin: "Google Home vs Amazon Echo: which smart home system is better?", Oct. 2019 http://www.pcadvisor.co.uk/review/digital-home/google-home-vs-amazon-echo-3648158/?p=2.
Tian, et al: "A comparative study of walking-induced dust resuspension using a consistent test mechanism", Indoor Air 2014; 24: 592-603, Wiley.

* cited by examiner

ALLERGEN WARNING SYSTEM AND METHOD

CROSS REFERENCE TO RELATED APPLICATIONS

This application is the U.S. National Phase application under 35 U.S.C. § 371 of International Application No. PCT/EP2019/064839 filed Jun. 6, 2019, which claims the benefit of European Patent Application Number 18176413.5 filed Jun. 7, 2018. These applications are hereby incorporated by reference herein.

FIELD OF THE INVENTION

This invention relates to an allergen warning system and method.

BACKGROUND OF THE INVENTION

The spread of respiratory allergies (allergic rhinitis) is increasing. Around one third of adults in the US has respiratory allergies and up to 40% of children in the US are allergic to respiratory allergens. Pollen is the perhaps the most common, although dust mites, mold and pet dander are also allergen sources for respiratory allergies.

According to the World Health Organization (WHO) there are currently 235 million people suffering from asthma worldwide. This number is on the rise.

Detecting asthma triggers and symptoms is a well-studied area. Tracking symptoms and indicators in exhaled breath compounds such as 8-isoprostane, carbon monoxide (CO), and other exhaled breath biomarkers is an approach for managing asthma by means of predicting and preventing asthma attacks. This approach can also extend to monitoring the physical indicators of asthma symptoms, such as tracking wheezing sounds with an on-body acoustic detector e.g. one or more microphones.

A broader approach is to incorporate environmental data as well, such as air quality and allergen/pollen indicators, for providing a better coverage of the patient management system, as well as generating location based advice and warnings.

Thus, various approaches are known for asthma warning systems, including using breath markers, tracking environmental conditions such as allergens/pollens, giving location based advice and sharing user feedback to a networked system.

Once contracted, renewed exposure to pollen can lead to exacerbations that in some cases can even lead to death.

Pollutants that an individual is exposed to such as pollen persist on clothes and shoes and can be a major cause of lower indoor air quality. This pollution source can affect multiple individuals who occupy shared spaces and can be a particular issue for individuals who are sensitive to outside pollutants such as pollen. The type of worn fabric and shaking of clothes can modify the amount of pollutants on an individual and their resuspension indoors.

Techniques exist to reduce the pollutants brought into a house involving manual shaking of clothes before entry, or immediate washing. Some automated products also exist that reduce the pollution brought into an internal environment by applying cleaning procedures to the shoes on entry. Manual techniques for reducing transmission of pollutants from an outdoor to an indoor environment rely on the individual to be aware of the pollutants they may be carrying, which they may not be, especially if they are not sensitive to the pollutant types they carry and not aware of the presence or sensitivities of other individuals in the indoor environment. Manual techniques are also only partially effective at reducing pollutant ingress.

Current products for automatic reduction of pollutants brought into an indoor environment are expensive and for example only reduce the pollutants from the shoes of individuals.

There is therefore a need to reduce the risk of allergen transfer to an indoor space, particularly when shared with other individuals, and which is more reliable and simple to implement.

WO 2017/148876 discloses a system for determining a risk level of a respiratory attack of a user, based on their activity levels and location, using information from other users.

US 2014/0213925 discloses another system for predicting respiratory episodes, based on a user's previous response to particular environmental conditions as well as the responses of other users of the system.

SUMMARY OF THE INVENTION

The invention is defined by the claims.

According to the invention, there is provided a system for warning of an exposure of a second individual to an allergen by transfer from a first individual, comprising:

a first user device for the first individual and a second user device for the second individual, each user device comprising a tracking system for tracking the movement of the respective individual;

a database which stores user sensitivity information to different allergens; and a controller which is adapted to:
 determine allergen types and levels to which the individuals have been exposed based on their movements; and
 determine if the first individual has been exposed to allergen types and levels which pose a risk to the second individual by allergen transfer from the first individual to the second individual.

The invention is based on the recognition that one approach for reducing an allergen risk to a user is to identify specifically the risk of transfer of allergens from one individual to another. This is possible because allergens and other pollutants that an individual is exposed to may persist on their clothes and shoes and then lower the indoor air quality of indoor spaces they enter.

This system aims to identify the specific scenario that a first user is exposed to an allergen which is a risk to a second user. It is of particular interest when the two users share a habitation space or work space. The first user may travel between work and home through a geographical area where there are allergens, e.g. pollen, which is a risk to a second user. When the first user arrives at work or at home, they may present a risk to the second user, who has not otherwise been exposed to that allergen. The system can then take active measures to prevent the transfer of the allergen between them. This may involve issuing a warning, so that the first user can clean their clothes, or the second user can avoid shared spaces, or an air treatment may be carried out.

The determination of whether the first individual has been exposed to allergen types and levels which pose a risk to the second individual (by allergen transfer from the first individual to the second individual) involves comparing the exposure information for the first individual with the user sensitivity profile for the second individual. A match is found if the first individual has been exposed to allergens which present a risk to the second individual based on their sensitivity profile.

The controller may be split in different ways between the user devices and a central system. In one example, each user device has a user device controller which determines the allergen types and levels to which the associated individual has been exposed based on their movements.

Each user device controller for example comprises an input for receiving geographical allergen information which relates to allergen types and levels from a remote source or from a database which is part of the user device. The user device may collect the allergen information wirelessly from a data source, such as a weather station, or it may maintain its own database, which is then updated based on collection of data from a network of sensors, for example.

Each user device may comprise a pollution sensor. In this way, the allergen information may be collected by the user device instead of or as well as obtaining external information.

Each user device may be adapted to provide a warning when the respective user has been exposed to allergen types and levels which pose a risk to that user. The user device thus may provide a warning of a direct allergen risk to that user, as well as a warning (or other action) relating to a risk of allergen transfer from the user to another user.

The controller may be adapted to provide a control signal for controlling an air treatment device in response to a determined risk. This provides an automatic measure to counteract the determined risk.

The controller may be adapted to provide a warning signal for warning the first and/or second users of the posed risk. This warning signal may be used by the users to change their behavior, for example to clean their clothes, enter a cleaning station (for example if the system relates to a hospital environment) or avoid the shared spaces.

The user devices may be adapted to communicate with each other and the controller is implemented by the user devices. Thus, the controller does not need to be part of a separate system to the user devices. It may be implemented by each user device in parallel, based on the exchange of data between the user devices.

Alternatively, the controller may comprise a system controller (in addition to local user device controllers) which is part of a central system which is separate to the user devices, wherein the user devices are adapted to communicate with the central system. The system controller is for example for positioning in a shared habitation space of the users. This may be a home or workplace or a hospital or other establishment. In this way, the central system monitors the presence of the users at the shared space.

The system may comprise a plurality of more than two user devices, wherein the controller is adapted to obtain the allergen types and levels and the user sensitivity information from all users, and thereby determine if any individual has been exposed to allergen types and levels which pose a risk to any other individual by transfer between them. The system for example provides monitoring of all users of a shared space.

The invention also provides a method for warning of an exposure of second individual to an allergen, and to which allergen the second individual is sensitive, by transfer from a first individual, comprising:

tracking the movement of the the first and second individuals;

determining allergen types and levels to which the individuals have been exposed based on their movements; and based on the allergen types and levels to which the individuals have been exposed and user sensitivity information to different allergens relating to the first and second users, determining if the first individual has been exposed to allergen types and levels which pose a risk to the second individual by allergen transfer from the first individual to the second individual.

This method specifically aims to identify a risk of allergen transfer from one individual to another, and particularly in a space which is shared by those users.

The movement tracking and determination of allergen types and levels may be implemented by user-carried user devices whereas the determination of a posed risk is performed either by communication between the user devices or by a central system, which is for example positioned in a shared space of the users, and which is separate to the user devices and with which the user devices communicate.

The method may comprise controlling an air treatment device in response to a determined risk and/or providing a warning signal for warning the first and/or second users of the posed risk.

The invention may be implemented at least in part in software, and the invention thus also includes a computer program comprising computer program code means which is adapted, when said program is run on a computer, to implement the method as defined above.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
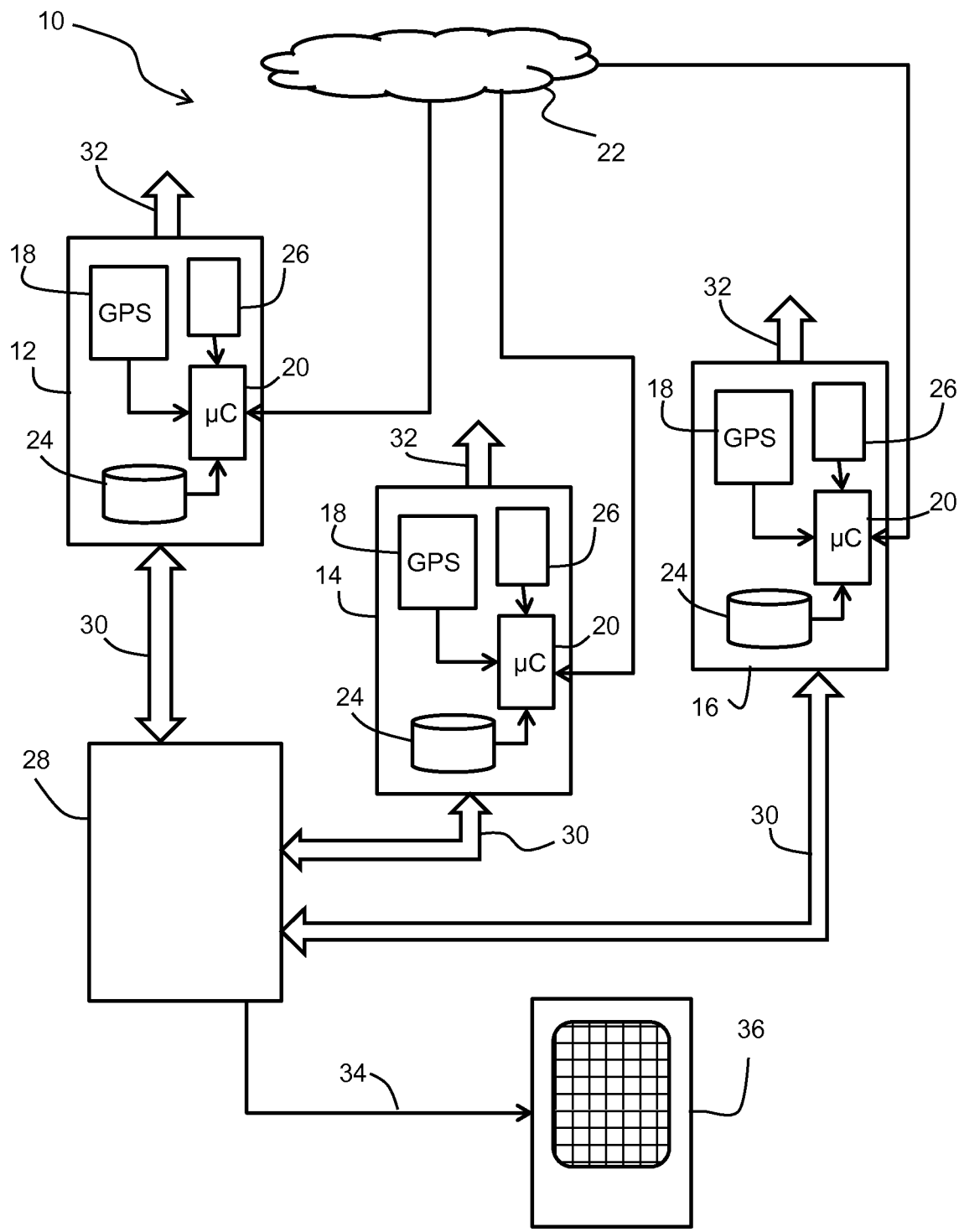
FIG. 1 shows a first example of a system for warning of a risk of exposure of a second individual to an allergen by transfer from a first individual.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a system and method for warning of an exposure of a second individual to an allergen by transfer from a first individual. Movements of the individuals are tracked so that allergen types and levels to which the individuals have been exposed can be obtained. Using knowledge of user sensitivity information to different allergens, it is determined if the first individual has been exposed to allergen types and levels which pose a risk to the second individual by transfer from the first individual to the second individual. Thus, action can be taken when there is a determined risk of allergen transfer between individuals.

FIG. 1 shows a system 10 for warning of an exposure of an allergen to a second individual by transfer from a first individual.

The system is for use by a set of users, and is for monitoring the users so that it can be determined if one user has been exposed to an allergen that may present an allergen attack risk for another user. FIG. 1 shows a system with three users, but there may generally be two or more users. Each user has a user device, so in the example shown there is a first user device 12, a second user device 14 and a third user device 16.

Each user device has a tracking system 18 such as a GPS system for tracking the movement of the respective individual. The location of an individual can be accurately tracked both indoors, using techniques such as Wi-Fi location tracking, or device motion tracking, and outdoors using GPS systems.

In this example, a device controller 20 is used for determining allergen types and levels to which the individual has been exposed based on their movements. For this purpose a geographical map of allergen types and concentrations is used. This map information may be obtained from an external source, such as over the internet 22 and/or from a local database 24. Map information in the local database may be updated based on information received from external sensors and for example from periodic updates, again performed by connection to external data sources over the internet. Thus, spatially and temporally resolved allergen (i.e. pollution) data is obtained.

The database additionally stores user sensitivity information to different allergens. This may be input manually by the user. It may for example comprise sensitivity ratings, for example on a scale of 1 to 10 to represent different pollutant concentrations which can be tolerated by the individual.

As explained below, only location tracking at the user device is required, since the other processing functions may be performed separately.

The user devices in this example also include an allergen sensor 26 which may be used either to generate the information of allergen types and levels or to supplement that information. Thus, one implementation may make use of only local sensors 26 with no need for external data, another implementation may make use of only external data, and another implementation may combine both sources of information. The allergen information may for example be crowd sourced.

The user devices may be implemented by smart phones or other portable devices.

The user devices store the determined allergen types and levels in memory, for example in the database 24. The memory may refresh old data after a certain time period, for example after a certain number of hours, after which that exposure information is no longer a risk factor.

Other information may be stored locally, for example the type of transport that has been taken (for example if the user been exposed others in public transport, if they drove or cycled or walked, etc.)

There is sharing of information between the user devices.

In the example of FIG. 1, there is a separate system controller 28 which is in bidirectional communication with the user devices, as shown by arrows 30. The role of the system controller 28 is to obtain the allergen types and levels and the user sensitivity information from the multiple user devices, and thereby determine if one individual (e.g. a first individual) has been exposed to allergen types and levels which pose a risk to any other individual (e.g. a second individual) by transfer from the one to the other.

The system controller 28 has a database of identities of registered users of the system. A list of user devices is for example obtained based on their connection to the local Wi-Fi network or by other short range communication means. The system controller queries each user device to obtain the sensitivity information (i.e. a sensitivity profile) and the allergen types and levels to which the user has been exposed (i.e. an exposure profile). This information is all stored in a database on the system controller. The exposure profiles and sensitivity profile of a user is not used when that user device is not found to be in the list current occupants.

When any new user device is added or leaves the shared area, the central controller compares the exposure profiles with the sensitivity profiles of all user devices currently in the shared space. The system controller aims to identify any potential conflict.

The invention is based on the recognition that one approach for reducing an allergen risk to an individual is to identify specifically the risk of transfer or allergens from another individual.

The system identifies the specific scenario that a first user is exposed to an allergen which is a risk to a second user. It is of particular interest when the two users share a habitation space or work space. The system controller in the example of FIG. 1 is thus located at the shared habitation or work space.

One user may collect allergens during their journey to and from work and then put other people who share their home or work space at risk. When a risk has been identified, this risk is alerted to the user devices from the central system. A user device may then provide a warning (shown generally as output 32) when the respective user has been exposed to allergen types and levels which pose a risk to others. Another user device may then provide a warning (again shown generally as output 32) when another user has been exposed to allergen types and levels which pose a risk to that user.

Thus, each of the two users may decide to take action. The exposed user may for example shake or remove their clothes before entering the shared space, or the at-risk user may vacate the shared areas for a time. The exposed user may for example operate a hand-held vacuum cleaner to clean their clothes, or may even be prompted to enter a cleaning area at the entry to a hospital or other clinical environment.

A user device may then also provide a warning when the respective user has been exposed to allergen types and levels which pose a risk to the same user. The user may not yet have noticed symptoms of their allergy, but can take action to limit their severity, for example by changing their clothes.

In addition to providing warnings, the system controller can then take active measures to reduce the risk of transfer of the allergen between users. For example, a control signal 34 may be provided for controlling an air treatment device 36 which is located in the shared space, in response to a determined risk. This provides an automatic measure to counteract the determined risk.

The system controller may provide control signals to select a type of filter to be use in the air treatment device, or to provide instruction to a user as to the type of filter that should be used. Different pollutants have different sizes and may therefore need different filters or filtration settings.

In order to determine the type of action to be taken, the system controller makes use of an algorithm for determining suitable measures to reduce allergen transferal, as discussed above. If multiple conflicts are found that would require different optimum action, such as different air treatment device settings, the sensitivity ratings of the different sensitivity profiles may be compared. The chosen action may for example be chosen to provide the greatest benefit to the most sensitive user.

In FIG. 1, only the user devices are shown generating a user output. The system controller may of course generate its own output as well, e.g. on a display panel or as an audible alarm.

Figure 2:
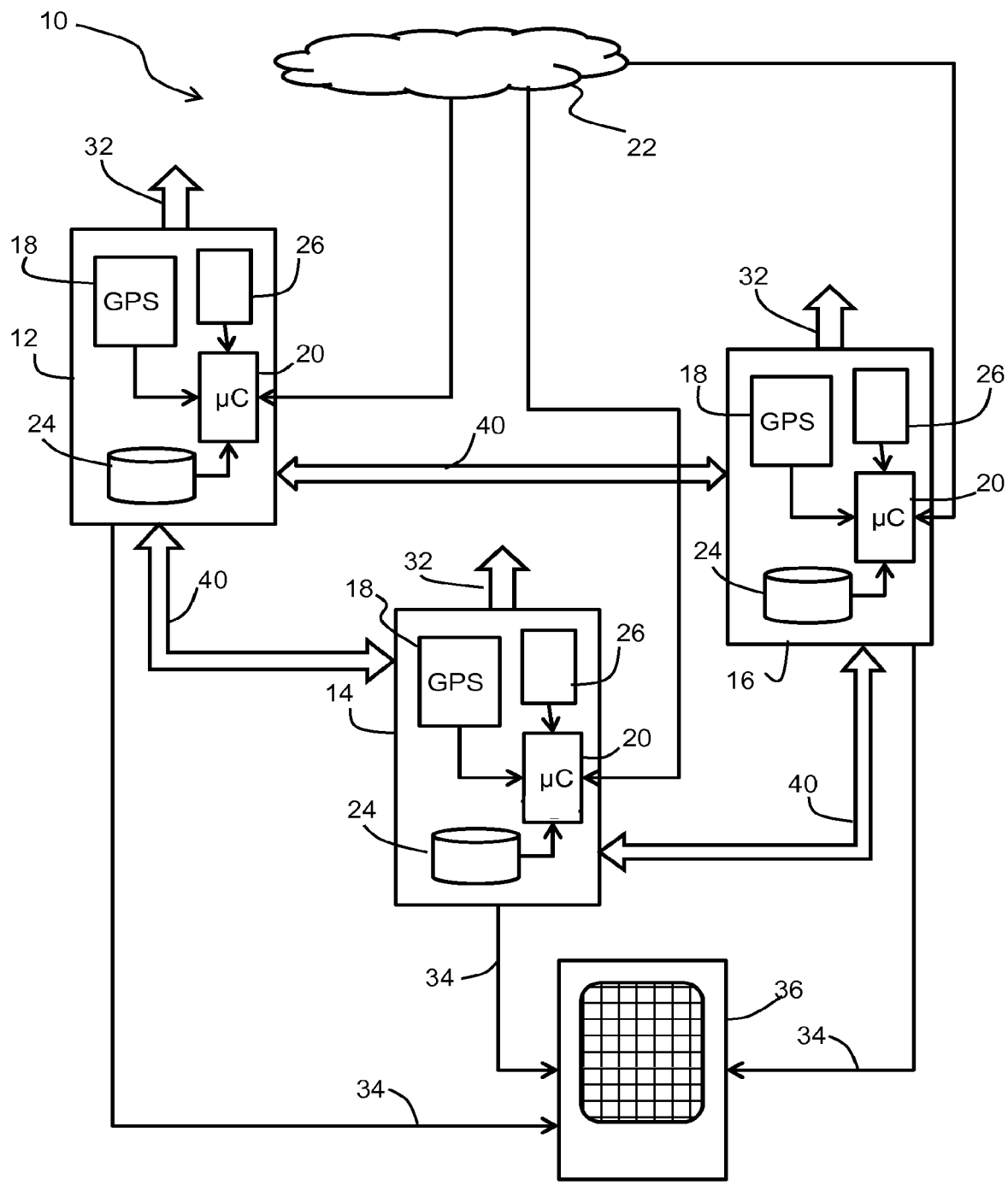
FIG. 2 shows a second example of the system.

FIG. 2 shows a modification to FIG. 1 in which the system controller is not a separate entity but is implemented by the user devices. The user devices communicate with each other as shown by arrows 40, so that they may each perform the central management tasks explained above. Each one may instruct the air treatment device 36. There is no central system controller.

There are various possible modifications to the system.

In the example above, the user device controller determines allergen types and levels to which the individual has been exposed based on their movements and it has the database which stores user sensitivity information to different allergens. However, these functions may be performed by the central system controller. Location data is stored by the user device over a certain period so that the exposure profile can then be obtained in the central system. This reduces the software requirements of the user devices.

The system may include regular users of the system, who come and go from the shared space. The sensitivity profiles of those regular users may be taken into account even when they are not present in the shared space, namely to prepare for their expected return to the shared space. Pollutants brought in by other users may persist for some time in the environment. The likely return of the regular user may be predicted based on known behavior or it may be known from current location information and movement information. Warnings may thus be provided in advance, or automatic cleaning actions may be taken in preparation.

There may be different levels of active measures and they may be different for different pollutant types. The active measures may be derived based on a calculation of an estimated deposited pollution dose.

A pollution dose may be calculated by applying a predetermined deposition factor to the average pollution level to which the user is exposed over a certain period of time (e.g. every 5 seconds) to estimate a proportion of the pollutant that is deposited on the user. This pollution dose may be summed over time and included in the user-specific exposure profile. A pre-defined shedding factor may also be applied to the pollutant dose over time. Optionally, the deposition and shedding factor may vary based on air or user conditions that affect these rates such as wind speed, pollutant types or worn fabric types. The shedding factor may also be calculated in proportion to the physical activity or movement recorded from the user.

This information may also be used to provide an indication that a user should not move too much in the shared space until they have cleaned their clothes. Alternatively, the risk estimation may take account of the likely amount of movement of that user and therefore the amount of allergen shedding likely in the shared space.

These additions would for example allow a more accurate prediction of possible negative reactions to a carried pollutant where each sensitivity level would have an associated trigger dose threshold. This may thus prevent an air treatment operation when it is not required.

Graded active measures (e.g. fan speeds) may be selected based on different levels of predicted reaction. If a very strong allergic reaction is predicted due to a high deposited dose of a particular pollen that is highly irritating to an individual, multiple actions may be taken such as:

notifying the exposed individual to take extra actions such as shaking their clothes before entering or removing shoes; and increasing the fan speed of an air purification device despite the cost of increased noise pollution.

In cases of smaller shared area, such as for different rooms in a house that in which different users reside or are currently present, occupancy can be defined using indoor location tracking systems such as Wi-Fi positioning systems for both the user and the central system controller. The shared area could then be defined by a 2 or 3 dimensional digital boundary which is used along with indoor location data about the user devices to determine the occupancy of the shared areas.

Figure 3:
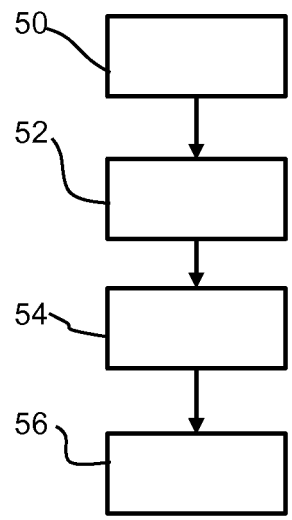
FIG. 3 shows a method for warning of a risk of exposure of a second individual to an allergen by transfer from a first individual.

FIG. 3 shows a method for warning of an exposure of a second individual to an allergen by transfer from a first individual, comprising:

in step 50, tracking the movement of the the first and second individuals;

in step 52, determining allergen types and levels to which the individuals have been exposed based on their movements; and in step 54, based on the allergen types and levels to which the individuals have been exposed and user sensitivity information to different allergens relating to the first and second users, determining if the first individual has been exposed to allergen types and levels which pose a risk to the second individual by transfer from the first individual to the second individual.

The movement tracking and determination of allergen types and levels may be implemented by user-carried user devices or else the user-carried user device may only provide location tracking and the associated with allergen information may be carried out by a central system controller.

The method may further comprise, in step 56, controlling an air treatment device in response to a determined risk and/or providing a warning signal for warning the first and/or second users of the posed risk.

As described above, the invention makes use of a controller, and the functionality may be split between multiple units.

Figure 4:
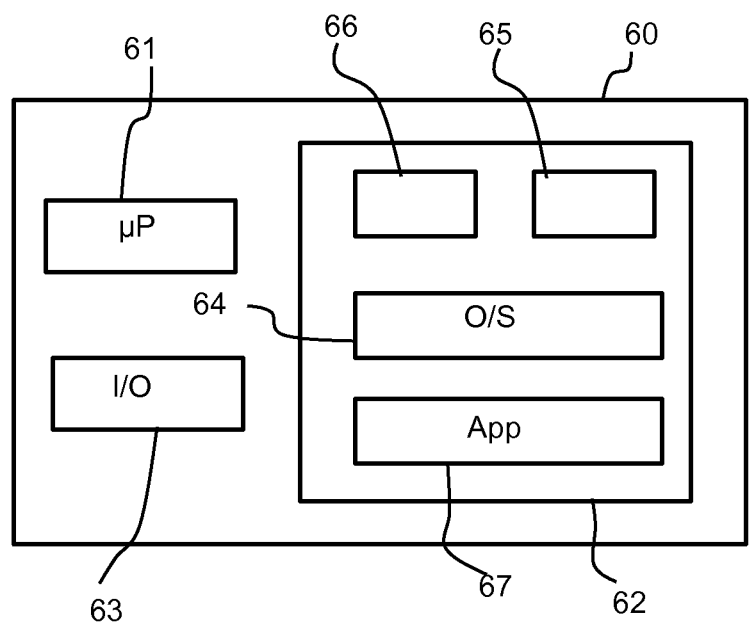
FIG. 4 illustrates an example of a computer for implementing the controller used in the systems of FIG. 1 or 2.

FIG. 4 illustrates an example of a computer 60 for implementing the controller or each controller unit described above.

The computer 60 includes, but is not limited to, PCs, workstations, laptops, PDAs, palm devices, servers, storages, and the like. Generally, in terms of hardware architecture, the computer 60 may include one or more processors 61, memory 62, and one or more I/O devices 63 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 61 is a hardware device for executing software that can be stored in the memory 62. The processor 61 can be virtually any custom made or commercially available processor, a central processing unit (CPU), a digital signal processor (DSP), or an auxiliary processor among several processors associated with the computer 60, and the processor 61 may be a semiconductor based microprocessor (in the form of a microchip) or a microprocessor.

The memory 62 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 62 may incorporate electronic, magnetic, optical, and/or other types of storage media. Note that the memory 62 can have a distributed architecture, where various components are situated remote from one another, but can be accessed by the processor 61.

The software in the memory 62 may include one or more separate programs, each of which comprises an ordered listing of executable instructions for implementing logical functions. The software in the memory 62 includes a suitable operating system (O/S) 64, compiler 65, source code 66, and one or more applications 67 in accordance with exemplary embodiments.

The application 67 comprises numerous functional components such as computational units, logic, functional units, processes, operations, virtual entities, and/or modules.

The operating system 64 controls the execution of computer programs, and provides scheduling, input-output control, file and data management, memory management, and communication control and related services.

Application 67 may be a source program, executable program (object code), script, or any other entity comprising a set of instructions to be performed. When a source program, then the program is usually translated via a compiler (such as the compiler 65), assembler, interpreter, or the like, which may or may not be included within the memory 62, so as to operate properly in connection with the operating system 64. Furthermore, the application 67 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 63 may include input devices such as, for example but not limited to, a mouse, keyboard, scanner, microphone, camera, etc. Furthermore, the I/O devices 63 may also include output devices, for example but not limited to a printer, display, etc. Finally, the I/O devices 63 may further include devices that communicate both inputs and outputs, for instance but not limited to, a network interface controller (NIC) or modulator/demodulator (for accessing remote devices, other files, devices, systems, or a network), a radio frequency (RF) or other transceiver, a telephonic interface, a bridge, a router, etc. The I/O devices 63 also include components for communicating over various networks, such as the Internet or intranet.

When the computer 60 is in operation, the processor 61 is configured to execute software stored within the memory 62, to communicate data to and from the memory 62, and to generally control operations of the computer 60 pursuant to the software. The application 67 and the operating system 64 are read, in whole or in part, by the processor 61, perhaps buffered within the processor 61, and then executed.

When the application 67 is implemented in software it should be noted that the application 67 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The invention is of particular interest in a system having multiple users, who are sensitive to particular pollutant types, and they share a space for example with one or multiple air purification devices and all carry a smart device that has determined their pollutant sensitivity information. The space is regularly entered by individuals who have been exposed to a variety of different pollutant types and who are carrying a user device of the system.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A system for warning of an exposure of a second individual to an allergen to which the second individual is sensitive by transfer from a first individual, comprising:
   a first user device for the first individual and a second user device for the second individual, each user device comprising a tracking system for tracking the movement of the respective individual;
   a database which stores user sensitivity information to different allergens; and
   a controller which is adapted to:
      determine allergen types and levels to which the individuals have been exposed based on their movements; and
      determine if the first individual has been exposed to allergen types and levels which pose a risk to the second individual by allergen transfer from the first individual to the second individual.

2. The system as claimed in claim 1, wherein the controller comprises a user device controller for determining the allergen types and levels to which the associated user has been exposed based on their movements, wherein the user device controller comprises an input for receiving geographical allergen information which relates to allergen types and levels from a remote source or from a database which is part of the user device.

3. The system as claimed in claim 1, wherein each user device comprises a pollution sensor.

4. The system as claimed in claim 1, wherein each user device is further adapted to provide a warning when the respective user has been exposed to allergen types and levels which pose a risk to that user.

5. The system as claimed in claim 1, wherein the controller is adapted to provide a control signal for controlling an air treatment device in response to a determined risk.

6. The system as claimed in claim 1, wherein the controller is adapted to provide a warning signal for warning the first and/or second users of the posed risk.

7. The system as claimed in claim 1, wherein the user devices are adapted to communicate with each other thereby together to implement the controller.

8. The system as claimed in claim 1, wherein the controller comprises a system controller which is part of a central system which is separate to the user devices, wherein the user devices are adapted to communicate with the system controller.

9. The system as claimed in claim 8, wherein the system controller is for positioning in a shared habitation or working space of the users.

10. The system as claimed in claim 1, comprising a plurality of more than two user devices, wherein the controller is adapted to obtain the allergen types and levels and the user sensitivity information from all users, and thereby determine if any individual has been exposed to allergen types and levels which pose a risk to any other individual by allergen transfer between them.

11. A method for warning of an exposure of an allergen to a second individual, and to which allergen the second individual is sensitive, by transfer from a first individual, comprising:
   tracking the movement of the the first and second individuals;
   determining allergen types and levels to which the individuals have been exposed based on their movements; and
   based on the allergen types and levels to which the individuals have been exposed and user sensitivity information to different allergens relating to the first and second users, determining if the first individual has been exposed to allergen types and levels which pose a risk to the second individual by allergen transfer from the first individual to the second individual.

12. The method as claimed in claim 11, wherein the movement tracking and determination of allergen types and levels are implemented by user-carried user devices.

13. The method as claimed in claim 11, wherein the determination of a posed risk is performed either by communication between the user devices or by a central system controller, which is for example positioned in a shared habitation or working space of the users, and which is separate to the user devices and with which the user devices communicate.

14. AThe method as claimed in claim 11, further comprising controlling an air treatment device in response to a determined risk and/or providing a warning signal for warning the first and/or second users of the posed risk.

15. A non-transitory computer readable medium comprising computer program code means which is adapted, when said program code is run on a computer, to implement the method of claim 11.

* * * * *